US008768027B2

(12) United States Patent
Chen et al.

(10) Patent No.: US 8,768,027 B2
(45) Date of Patent: Jul. 1, 2014

(54) METHOD AND SYSTEM FOR CONE BEAM COMPUTED TOMOGRAPHY HIGH DENSITY OBJECT ARTIFACT REDUCTION

(75) Inventors: Shoupu Chen, Rochester, NY (US); Lawrence A. Ray, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 658 days.

(21) Appl. No.: 12/710,522

(22) Filed: Feb. 23, 2010

(65) Prior Publication Data

US 2011/0206258 A1    Aug. 25, 2011

(51) Int. Cl.
*G06K 9/00* (2006.01)
*A61B 6/00* (2006.01)
*G06T 7/00* (2006.01)

(52) U.S. Cl.
CPC ..... *G06T 7/0012* (2013.01); *G06T 2207/10081* (2013.01)
USPC ............................................. 382/131; 378/4

(58) Field of Classification Search
CPC ........................................ G06T 7/0012–7/0016
USPC .......................................... 982/131; 382/131
See application file for complete search history.

(56) References Cited

U.S. PATENT DOCUMENTS

| 6,094,467 A * | 7/2000 | Gayer et al. ...................... 378/4 |
| 6,721,387 B1 | 4/2004 | Naidu et al. |
| 7,023,951 B2 * | 4/2006 | Man .................................. 378/8 |
| 2003/0103595 A1 * | 6/2003 | Raupach ........................... 378/4 |

FOREIGN PATENT DOCUMENTS

WO    WO 2006/082563    8/2006

OTHER PUBLICATIONS

Zhang-O'Connor Y. Noise properties of regularized image reconstruction in X-ray computed tomography. [Order No. 3287670]. University of Michigan; 2007.*
European Search Report, Application No. EP 11 001 412.3, mailed Jun. 14, 2011, 3 pages.
Hengyong Yu, et al., "A Segmentation-Based Method for Metal Artifact Reduction," Academic Radiology, vol. 14, No. 4, Apr. 2007, pp. 495-504.
M. Abdoli, et al., "Reduction of Dental Filling Metallic Artifacts in CT-Based Attenuation Correction of PET Data Using Weighted Virtual Sinograms," 2009 IEEE Nuclear Science Symposium and Medical Imaging Conference, pp. 2752-2755, XP031826584.
Koji Kobayashi, et al., "A Practical Method to Reducing Metal Artifact for Dental CT Scanners," 19$^{th}$ International Conference on Pattern Recognition, 2008, pp. 1-4, XP031412333.

(Continued)

*Primary Examiner* — Sheetal R Rangrej

(57) ABSTRACT

A method of providing a corrected reconstructed computed tomography image accesses image data for computed tomography images of a subject, identifying a subset of the computed tomography images that contain high density features. At least one high density feature is detected in each of the identified subset. The high density feature is classified and a compensation image is formed by distributing pixels representative of tissue over the classified high density feature. A difference sinogram is generated for each image in the identified subset of images by subtracting a first sinogram of the high density feature from a second sinogram of the original image. A resultant sinogram is generated for each image in the identified subset by adding a third sinogram generated according to the compensation image to the difference sinogram. The corrected reconstructed computed tomography image is formed according to the resultant sinogram generated for each image in the identified subset of images.

16 Claims, 15 Drawing Sheets

(56) References Cited

OTHER PUBLICATIONS

Yutaka Takahashi, et al., "Preliminary Study of Correction of Original Metal Artifacts due to I-125 Seeds in Postimplant Dosimetry for Prostate Permanent Implant Brachytherapy," Radiation Medicine, vol. 24, No. 2, pp. 133-138, 2006.

Yinsheng Li, et al., "Metal Artifact Reduction in CT Based on Adaptive Steering Filter and Nonlocal Sinogram Inpainting," 2010 3$^{rd}$ International Conference on Biomedical Engineering and Informatics (BMEI 2010), Oct. 16, 2010, pp. 380-383, XP031804056.

"Artifacts in Spiral X-ray CT Scanners: Problems and Solutions", *Proceedings of World Academy of Science, Engineering and Technology*, vol. 26, Dec. 2007, pp. 376-380) researcher Mehran Yazdi.

\* cited by examiner

US 8,768,027 B2

METHOD AND SYSTEM FOR CONE BEAM COMPUTED TOMOGRAPHY HIGH DENSITY OBJECT ARTIFACT REDUCTION

FIELD OF THE INVENTION

The invention relates generally to image processing in x-ray computed tomography (CT) and, in particular, to reducing image artifacts in image reconstruction due to metal or other high density materials.

BACKGROUND OF THE INVENTION

There are various artifacts that are characteristic to computed tomography (CT) technology, for example, such as in cone beam CT (CBCT) and spiral x-ray CT. In one paper ("Artifacts in Spiral X-ray CT Scanners: Problems and Solutions", *Proceedings Of World Academy Of Science, Engineering and Technology*, Volume 26, December 2007, pp. 376-380) researcher Mchran Yazdi describes three classes of artifacts: physics-based, patient-based, or scanner-based artifacts. Physics-based artifacts, for example, can be caused by beam hardening, photon starvation, and under-sampling. Patient-based artifacts can include artifacts caused by high density objects and inadvertent motion. Scanner-based artifacts include those caused by detector sensitivity and mechanical instability.

Artifacts caused by metal and other high density materials pose a significant problem that affects the performance of computed tomography (CT) systems. Metal features tend to generate high-frequency streaks or artifacts in the resulting image, typically emanating from metal objects in the scanned subject. These artifacts could occur due to high attenuation by the metal objects and consequent reduction in the number of photons reaching the detector of the CT system. This can also result in a poor signal-to-noise ratio. Additionally, metal objects harden the x-ray beam by attenuating x-rays in an energy-specific manner. The resulting nonlinear changes in the projection data can appear as low-frequency tail artifacts around the metal objects, as well as between the metal and other high density objects. For example, in medical diagnostic imaging, streaks caused by implanted metal objects limit the capability to assess surrounding soft tissues and skeletal structures. In dental cone beam CT imaging, artifacts cased by dental fillings (including dental fixtures) can constrain or prevent proper representation of surrounding tooth, bone, and tissue structures. Metal and other high density features attenuate x-ray beams as they propagate through the patient or other subject being exposed, complicating the task of accurate 3-D reconstruction and often resulting in unwanted image artifacts.

Various approaches have been considered to mitigate the effects of high density objects in CT reconstruction. One simple preventive solution has been to use filling and restorative materials that have lower X-ray attenuation coefficients and to develop and use implants and other devices that have smaller cross-sectional areas. Another approach is increasing the X-ray energy to improve beam penetration and to reduce effects of the missing projection data resulting from high density features. These approaches can help to reduce/minimize the impact of Metal and other high density features, but may not be appropriate in all cases. Increasing X-ray energy, because of increased risk to the patient, is seen as a poor solution to the problem.

Image processing methods have been developed to address the artifact problem. One method for addressing artifacts due to high density features is to reformat the axial CT image data into new interpolated axial, orthogonal, or oblique images. Image reformatting into planes other than the scan plane can weight the true image signal over the pseudo randomly distributed artifact signal when integrating between adjacent axial images (original axial images are averaged out of the planar reformatting). As another processing solution, post-reconstruction filtering can also be directly applied to noisy images to improve image quality.

Image processing methods that have been considered for reducing artifacts and re-creating the missing projection data can be generally classified into two categories: projection interpolation and iterative reconstruction. As one example of the latter approach, U.S. Pat. No. 7,023,951 entitled "Method and Apparatus for Reduction of Artifacts in Computed Tomography Images" to Man describes a method for reducing artifacts in CT images by iteratively reconstructing corrected sinogram data to generate improved reconstructed CT images based on a weight measure associated with each sinogram element. The corrected sinogram is generated by, for example, interpolating a measured sinogram that is the original sinogram obtained from the CT scanner.

Non-iterative sinogram interpolation techniques have also been proposed for addressing this problem. For example, U.S. Pat. No. 6,721,387 entitled "Method and System for Reducing Metal Artifacts in Images Generated by X-ray Scanning Devices" to Naidu et al. describes identifying metal objects in preliminary images, generating metal projections from the identified metal objects, then subtracting the metal projections from the input projections to yield corrected projections. The final corrected image is then reconstructed from the corrected projections. Naidu et al. also describe preserving thin-sheet high density objects in the '387 patent disclosure.

Conventional image processing methods that address the metal artifact problem use information extracted from neighbors of the high density objects identified to mitigate the artifacts. While such methods may have some merit, however, they fall short of what is needed for accurate artifact compensation for cone-beam CT dental images. A number of problems encountered in dental CT imaging are particular to dental imaging applications and are not encountered for other imaging applications. For example, unlike other CT imaging applications, dental CT imaging encounters a range of hard and soft tissue types, such as hone, dentine, enamel, and gum tissue, as well as a variety of metals and other high density materials used in fillings, implants, crowns, and other restorative structures. Interpolation methods such as those proposed in the Naidu et al. '387 disclosure can be employed when metal objects are embedded within a substantially homogenous area, but yield disappointing results in the dental imaging environment where metal objects or fillings reside in regions that have dramatically different properties than the surrounding tissues. In general, automated procedures for metal detection can be computationally intensive and may not utilize relevant information about the patient in order to optimize operation.

Thus, Applicants recognize that there is a need for a method that compensates for artifacts due to metal and other high density materials in CBCT and other CT scanning, particularly dental CT scanning.

SUMMARY OF THE INVENTION

It is an object of the present invention to advance the art of metal artifacts reduction in computed tomography reconstruction. With this object in mind, the present invention provides a method of providing a corrected reconstructed computed tomography image, executed at least in part on a computer processor and comprising: accessing image data for a plurality of computed tomography images of a subject; identifying a subset of the computed tomography images that contain one or more high density features; detecting, in each of the identified subset of computed tomography images, at least one high density feature; classifying the at least one high density feature according to one or more feature characteristics; forming one or more compensation images by distributing pixels representative of tissue over the at least one classified high density feature; generating a difference sinogram for each image in the identified subset of images by subtracting a first sinogram of the at least one high density feature from a second sinogram of the original image; generating a resultant sinogram for each image in the identified subset of images by adding a third sinogram generated according to the one or more compensation images to the difference sinogram; and forming the corrected reconstructed computed tomography image according to the resultant sinogram generated for each image in the identified subset of images.

A feature of the present invention is interaction with an operator to inform the imaging system of particular areas for artifact compensation according to patient characteristics.

An advantage of the present invention is its capability to direct metal artifact correction processing to only that portion of a reconstructed CT image where this is required.

Embodiments of the present invention, in a synergistic manner, integrate skills of a human operator of the system and knowledge of patient history with computer capabilities for metal artifacts reduction. This takes advantage of human skills of creativity, use of heuristics, flexibility, and judgment, and combines these with computer advantages, such as speed of computation, capability for exhaustive and accurate processing, and reporting and data access capabilities.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

The foregoing and other objects, features, and advantages of the invention will he apparent from the following more particular description of the embodiments of the invention, as illustrated in the accompanying drawings.

DETAILED DESCRIPTION OF THE INVENTION

Figure 1:
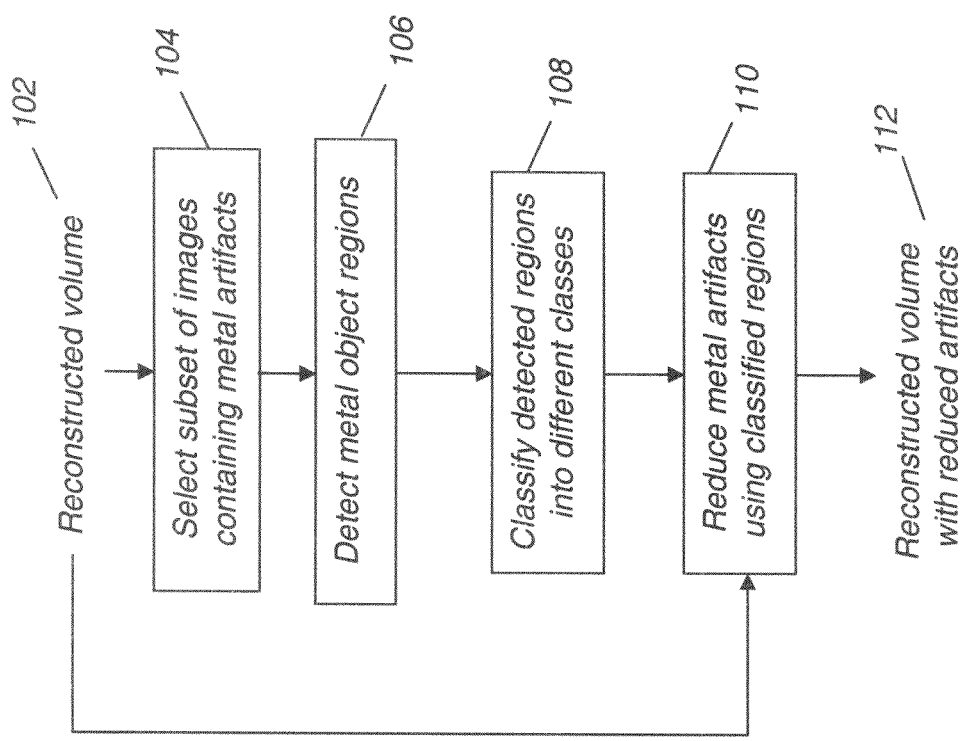
FIG. 1 is a logic flow diagram showing processes of the present invention in one embodiment.

In the following detailed description of embodiments of the present invention, reference is made to the drawings in which the same reference numerals are assigned to identical elements in successive figures. It should be noted that these figures are provided to illustrate overall functions and relationships according to embodiments of the present invention and are not provided with intent to represent actual size or scale.

In the context of the present invention, the descriptive term "high density feature(s)" generally indicates a region, mass, or object of metal or other material, such as a tilling material that exceeds the density of the surrounding tissue and would be identified as a high density feature by a skilled practitioner. As just one example of a high density material, aluminum has a density value in excess of about 2.7 $g/cm^3$. Because of differences related to dosage, however, it is impractical to posit any type of absolute threshold for defining high density; in any particular image, a high density feature may have a Material density value that is well below that exhibited by aluminum or other metals. Moreover, while subsequent description primarily describes metal features, it should be emphasized that the detection of high density features and correction of corresponding artifacts also applies for non-metal high density materials.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S.

Where they are used, the terms "first", "second", and so on, do not necessarily denote any ordinal or priority relation, but may be simply used to more clearly distinguish one element from another.

The subject matter of the present invention relates to digital image processing and computer vision technologies, which is understood to mean technologies that digitally process data from a digital image to recognize and thereby assign useful meaning to human-understandable objects, attributes or conditions, and then to utilize the results obtained in further processing of the digital image. The process of forming an image in digital image processing is understood to comprise forming image data and storing the formed image data in electronic memory for future access, including subsequent processing and display.

Unlike conventional methods for addressing the difficulties caused for CT imaging by metal and other dense features, the method of the present invention reduces artifacts caused by the high density features using classification of regions that are occupied by the high density features in order to correct the original projection images, and then reconstructs the CT images with the corrected projection images.

Referring to the logic flow diagram of FIG. 1, there is shown a sequence of steps used for metal artifacts reduction for a dental CBCT volume in one embodiment. A volume contains image data for one or more images (or equivalently, slices). An original reconstructed CT volume 102 is formed from electronically stored image data using standard reconstruction algorithms using multiple projections or sinograms obtained from a CT scanner. Normally, only a fraction or subset of the images that form the volume contain high density or metal objects; the rest of the CT reconstructed volume accurately represents tooth or soft tissue, without metal or other high density features. The metal artifacts reduction procedure, relatively costly in terms of time and needed computation resources, is only required for a few selected images. This selection of a subset of images for this procedure is done in an image selection step 104. In a metal features detection step 106, features for metal objects are detected in each of the selected images from step 104. Then, unlike conventional methods, the regions occupied by the detected metal features are classified in a classification step 108 before being used to reduce artifacts in an artifact reduction step 110. The end-result of this processing is a reconstructed volume 112 having reduced artifacts as output of the image processing.

Selecting a Subset of Images

Embodiments of the present invention improve the overall efficiency and effectiveness of artifact reduction by targeting only the subset of images used for CT reconstruction that include a high density feature. This subset can be identified using automated techniques, as described herein, or may be identified by instructions from the system operator, as described subsequently.

Figure 2:
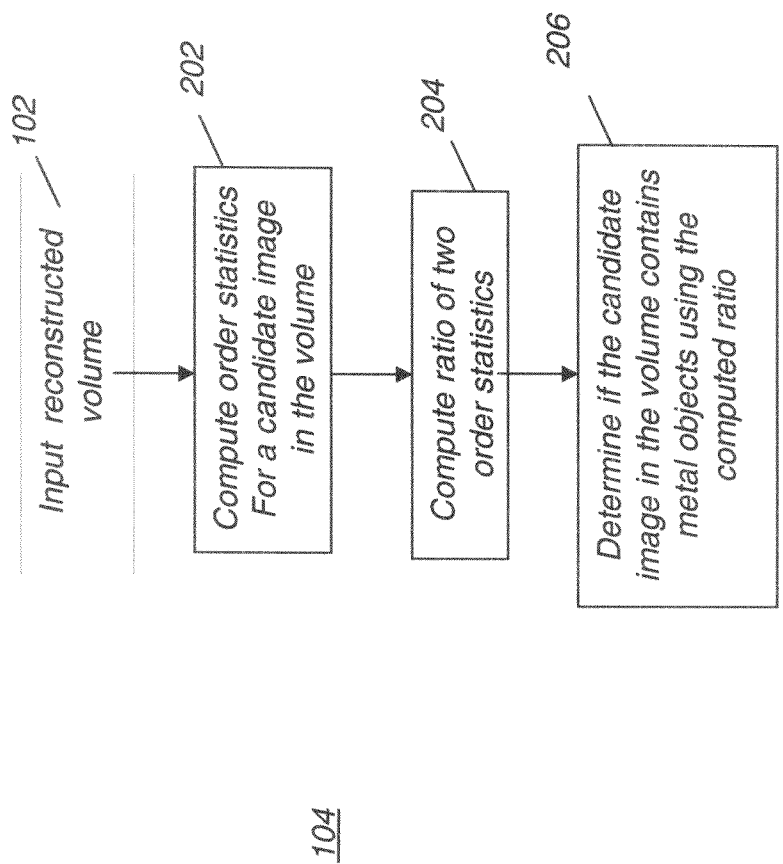
FIG. 2 is a logic flow diagram showing processing for detecting a subset of images with high density features in one embodiment.

An automated method for image selection step 104 in the above workflow is described in more detail in the flowchart shown in FIG. 2. This procedure utilizes order statistics obtained from original reconstructed CT volume 102. Order statistics provides a non-parametric statistical tool that is useful for addressing data analysis problems such as population composition analysis. Techniques that use order statistics consider the sampled variables arranged in order of value. For image analysis, order statistics considers each pixel value k ranging from 0 . . . n for an image (or slice) in the original reconstructed CT volume 102 as one of a collection or set of samples from a poll, arranged in order of intensity value. Embodiments of the present invention then process and analyze the order statistics to determine whether or not an image contains metallic or other high density objects.

Referring to FIG. 2, a sequence is shown that is executed for each image in the volume as a "candidate" image for selection as member of the subset. In a computation step 202, pixels within each candidate image are first sorted (ordered) according to their intensity values, to provide these values in the form of order statistics. Then, a number of order statistics are computed in step 202 for subsequent processes. Exemplary order statistics used in embodiments of the present invention include the set maximum and set median values. The ratio of two order statistics is then computed in a ratio computation step 204. In an evaluation step 206, the ordered collection of the ratios of the set maximum and other computed order statistics, including the set maximum itself, are examined, evaluating the candidate image to provide useful information about the image content. As a result of this evaluation, the candidate image may be selected as a member of the subset of images that contain a high density feature.

Figure 3:
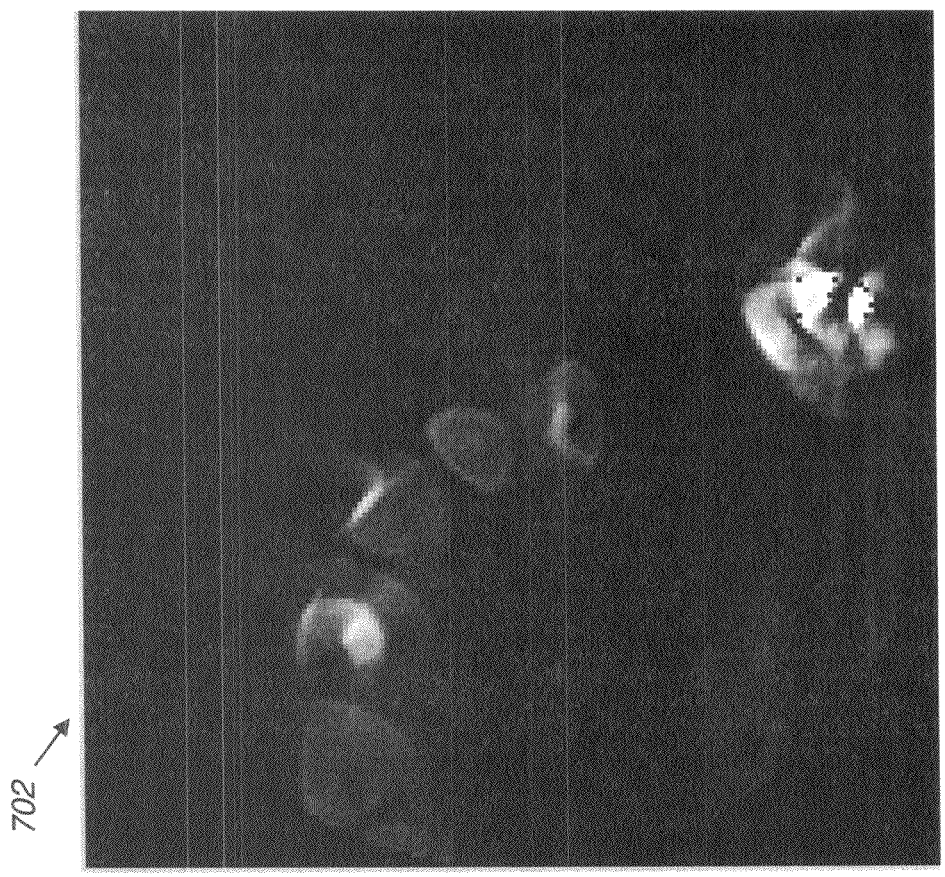
FIG. 3 is a view of a reconstructed CBCT image having artifacts due to high density features.
Figure 4:
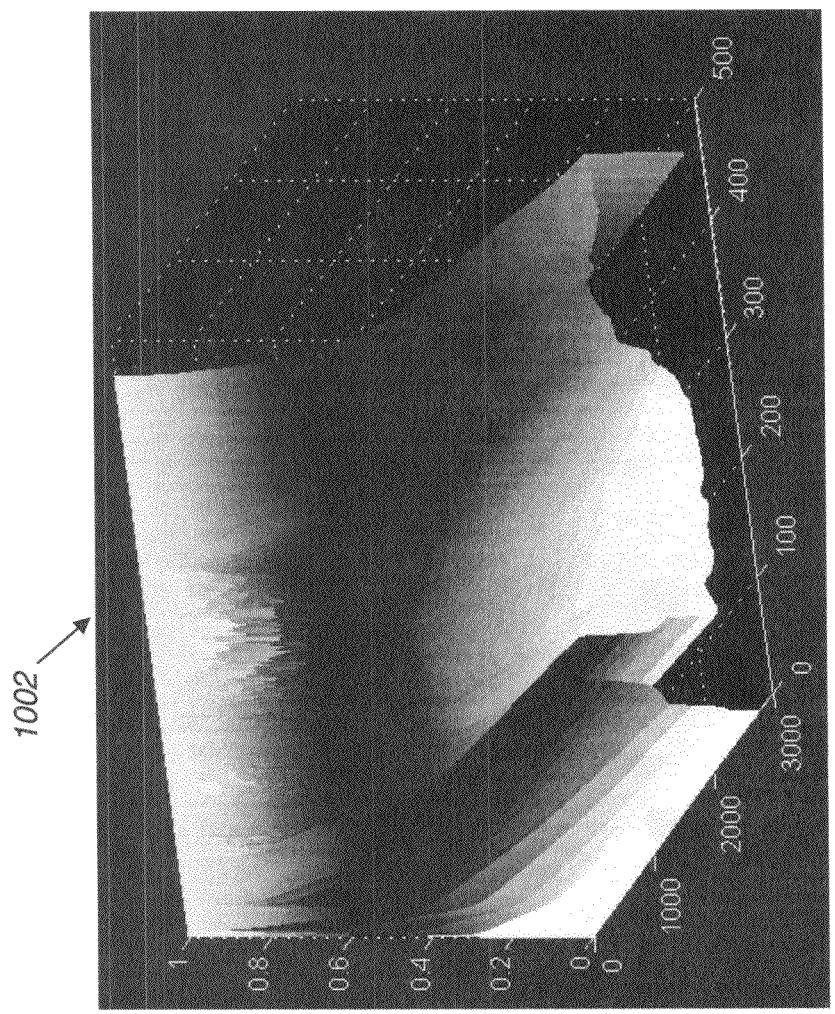
FIG. 4 is a view of a surface formed from ratios of order statistics to maximum intensity for the images in a reconstructed CBCT volume.
Figure 5:
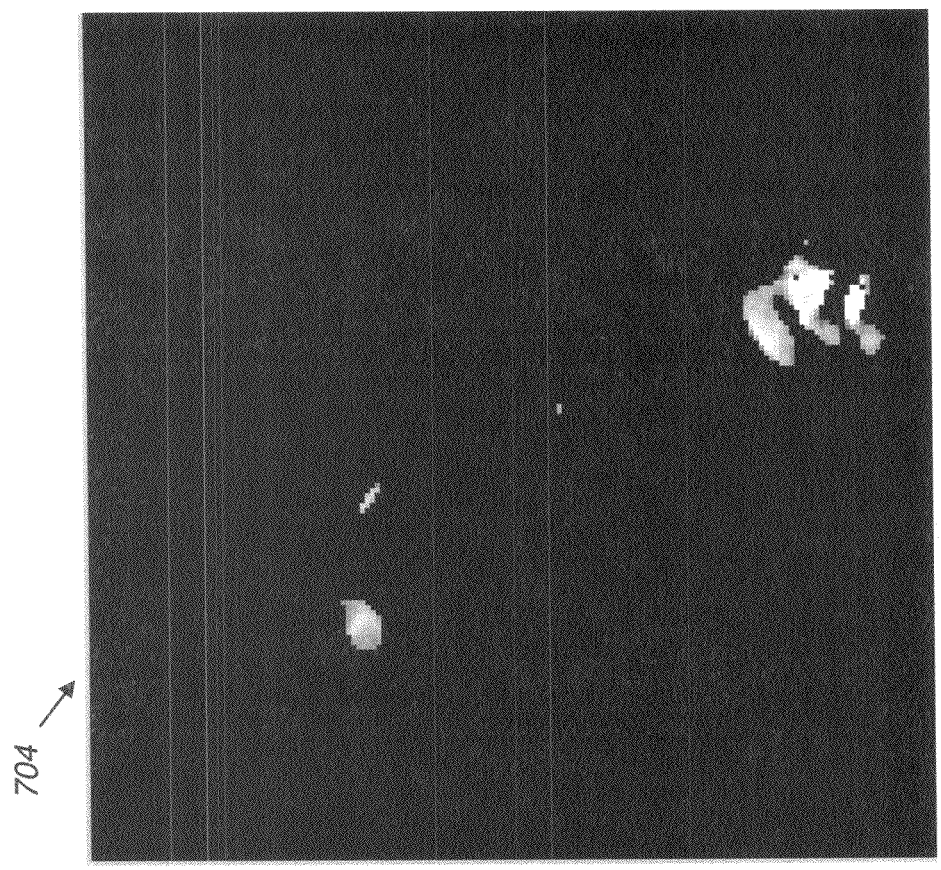
FIG. 5 is an example of a high density features image.

By way of example, the sequence of FIGS. 3, 4, and 5 show how image selection step 104 of FIG. 1 is carried out for selecting a suitable reconstructed CT volume 102 using an automated process. FIG. 3 shows a selected original reconstructed CT image 702, an exemplary dental image in which dental fillings and corresponding image artifacts are visible. Following the sequence of FIG. 2, order statistics are computed in computation step 202. For each slice of the reconstructed CT volume, this step generates an ordered set of intensity values, arranged in order, and computes maximum, median, and other values for the set. Then, in step 204, the ratio of each value in the set of order statistics to the maximum is computed.

FIG. 4 shows a 3-dimensional graph 1002 of a portion of the surface formed by curves of the ratios of the order statistics to the set maximum, with values considered down to the set median, for slices 1 to 470 of the reconstructed CT volume. The vertical axis represents the computed ratio. The axis numbered 0 to 500 represents the slice number for each slice in the volume. The axis that is orthogonal to the vertical ratio axis and numbered 1000, 2000, 3000 gives the index (k) for the ratio that applies to each corresponding (kth) order statistic. In the representation of FIG. 4, only the upper portion of the ratio data for each slice is represented; ratios of the set maximum and order statistics below the set median are of less interest and are not shown. It is clear from FIG. 4 that each curve begins with a value of 1, then decays, with varying curvature as the ratio drops for additional values. It should be noted that the curves for different slices generally differ from each other unless there are identical images within a volume.

The analysis visually described using FIG. 4 helps to identify volume slices that include metallic or other high density materials. A depression or trough in the surface is indicative of highly dense features. In FIG. 4, for example, the trough extending from about slice 90 to about slice 300 corresponds to a portion of the CT volume that contains dental fillings that are dense to x-ray radiation. Using this type of analysis to determine automatically whether an image contains high density objects, the ratio of the set maximum and the set median is used as a criterion for carrying out evaluation step 206 in FIG. 2. If the ratio of the set maximum and the set median for an image is below a ratio threshold value of 0.2, for example, that image very likely has metal or other high density feature content and is thus a good candidate image for membership in the subset of images that is to be processed in subsequent steps. Image 702, shown in FIG. 3 is such an exemplary dental image in which dental fillings are visible. It can be appreciated that computation of ratios for one or more order statistics is one of a number of useful methods for quickly determining whether or not a candidate image should be part of the subset of images containing high density features. Empirically, a threshold value near 0.2 appears to be a useful indicator of high density feature content when using such a ratio, but other threshold values could be used. Other methods for profiling and evaluating pixel values within each volume slice can alternately be applied.

Referring again to FIG. 1, a number of steps follow once the subset of images containing metal or other high density features is selected. The selected image from step 104 is first processed to detect metal object features or other high density object features in detection step 106. A metal object feature or region is a non-empty set of metal object pixels with the property that any pixel in the feature is also within a predefined distance to another pixel in that feature. One exemplary value of a predefined distance is 1.0 pixel.

Thresholding provides one method for identifying a metal object feature or other high density object feature. Pixels in image 702 of FIG. 3, for example, whose intensity values are above a predetermined intensity threshold value are saved as part of a high density features image. In one embodiment, the threshold value is set as a certain percentage of the set maximum for that particular image. An exemplary percentage could be 90%, the threshold value equal to 0.9 times the maximum intensity value. For the example image shown in FIG. 3, a resulting high density features image 704 shown in FIG. 5 shows metallic or other high density features resulting from applying metal detection step 106 to image 702. As can be seen, high density features image 704 in FIG. 5 contains a number of high density object features or regions, here, dental fillings. This provides a measure of image segmentation that is useful for subsequent processing steps.

Classification

One obstacle to the use of conventional metal artifact reduction techniques for dental CBCT applications relates to the diverse types of tissue that are involved in dental imaging. As discussed in the background section, conventional methods use information extracted from neighboring pixels of high density objects to reduce artifacts caused by metal objects. In the conventional approach, a mis-projection (that is, an integration along an X-ray path that is interrupted by the metal object) is interpolated using neighboring projections (integration along X-rays that are not interrupted by the metal object). This approach works fine in a situation where the tissues covered or replaced by a metal object have the same properties as the tissues immediately surrounding the metal object. This is, however, not true in dental filling cases, as noted in the Background section given earlier. One example is the dental root canal The tissue (root canal) covered or occupied by the filling material is totally different from the surrounding tissue (dentins). Therefore, the projections used in the interpolation process may contain components of incompatible densities.

Figure 6:
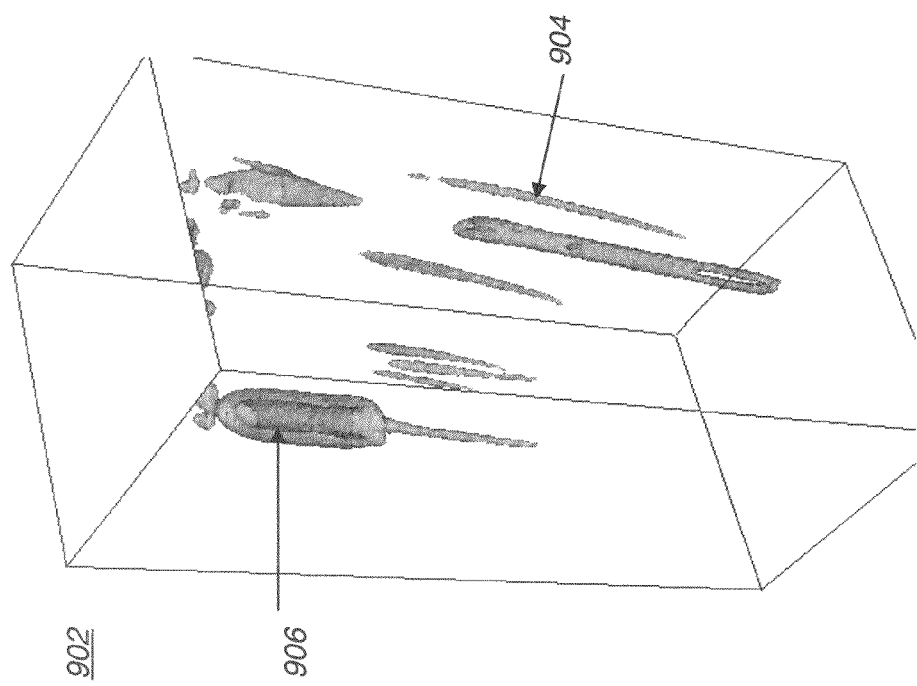
FIG. 6 is an example of an exemplary dental volume showing high density features.

FIG. 6 depicts a three dimensional display 902 of an exemplary dental volume that helps to show the problem that classification addresses. Display 902 includes two types of high density metal features. For example, a feature 906 is a filling that can be classified as a dentine-class filling. A second type of feature 904 shows a filling that can be classified in the root-canal class. Criteria used for automated classification of high density features can include various feature characteristics, including dimensional, positional, and geometric measurements of the features. This can include, for example, feature diameter, feature length and orientation, and feature position relative to other features or regions of the tooth or to the volume itself.

Classification can be provided using an automated process that evaluates each high density feature that is detected according to measured positional, geometric, or other characteristics. Alternately, classification can be obtained according to operator-entered information. Once a particular high density feature has been classified, the appropriate artifact correction processing can be applied.

Forming a Compensation Image

Figure 7:
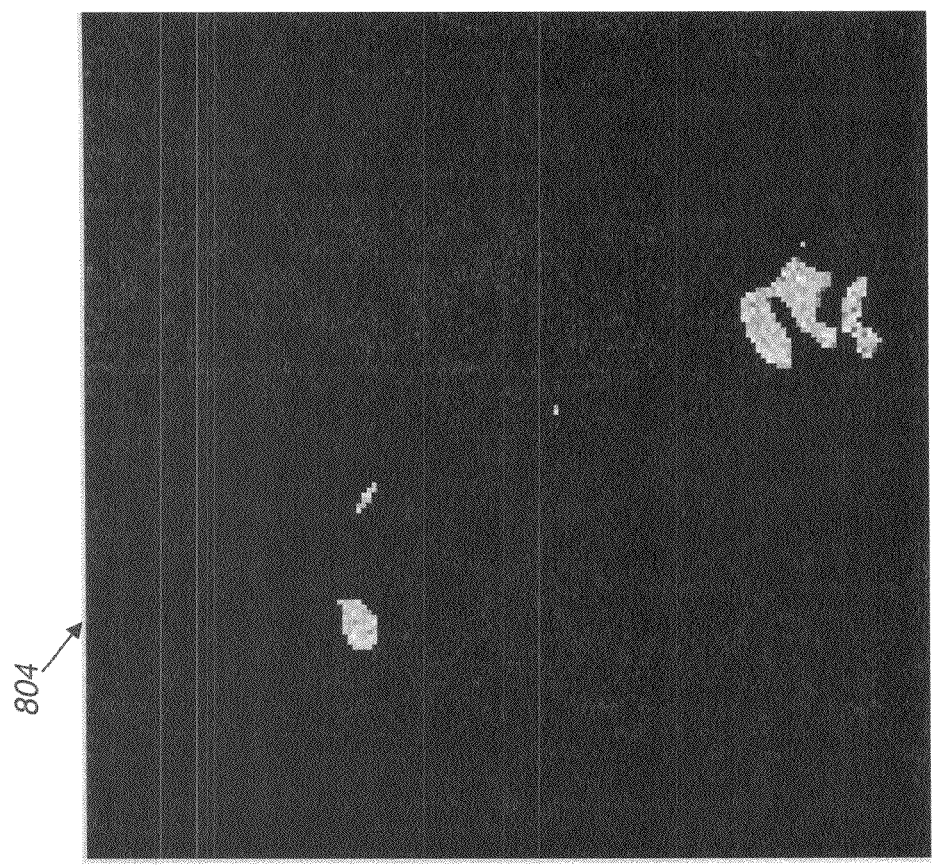
FIG. 7 is an example of a compensation image formed using the high density features image of FIG. 5.

Once the subset of images having the high density feature (s) has been identified, the high density features image 704 obtained, and the feature classification defined, a compensation image for use in artifact reduction can be formed. Referring to FIG. 7, there is shown a compensation image 804 that is formed by distribution of dentine pixels over segmented areas of high density features image 704. For this purpose, sample values of representative dentine pixels for substitution are collected beforehand from a plurality of dental images and used to generate compensation image 804. Sample dentine pixels can he cropped as a patch from a library of sample stored dental images, for example. Sample dentine pixels are randomly planted in image 804 in regions corresponding to those in image 704. In general, statistically learned values can be used for providing the representative substitution pixels in the compensation image.

Reconstruction with Artifact Correction

Figure 8:
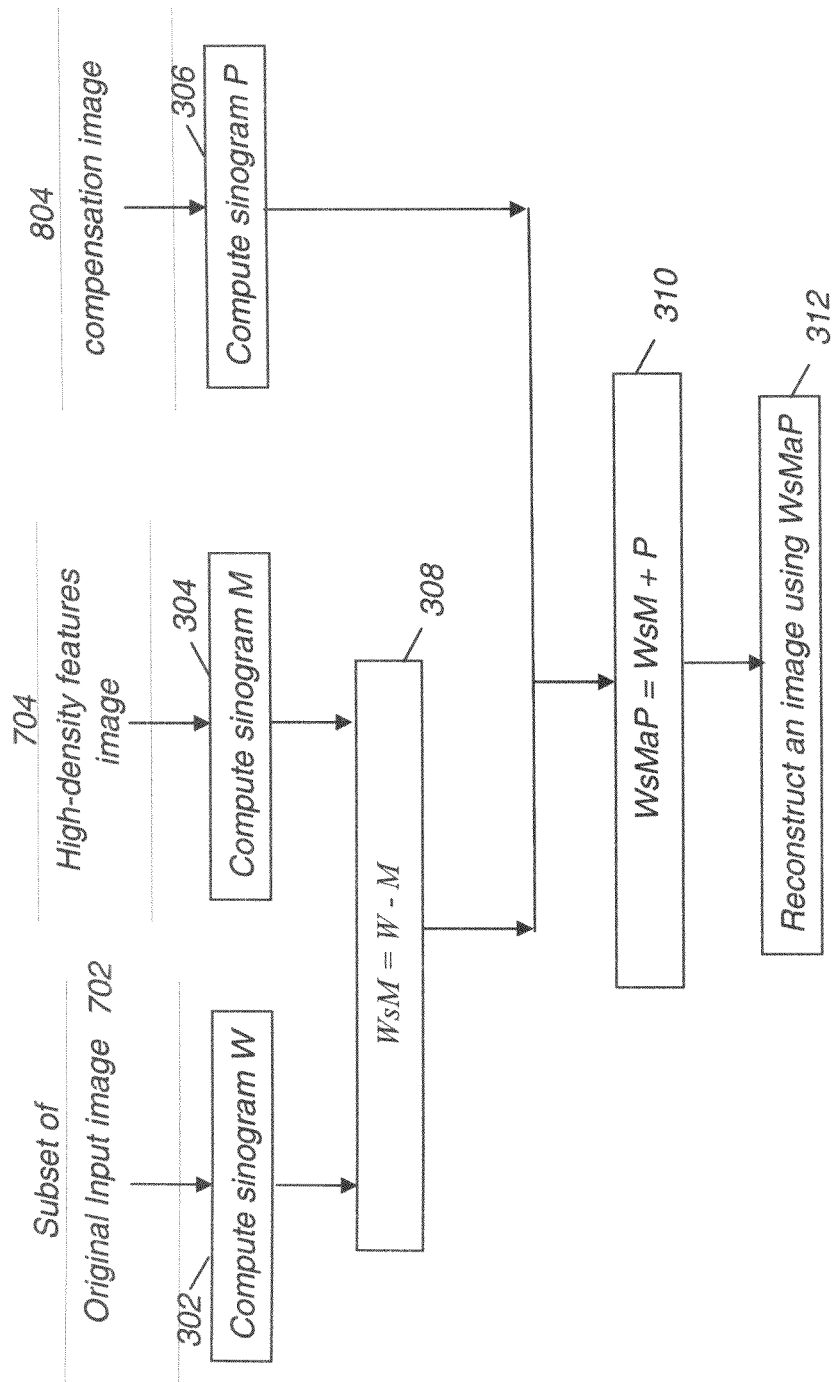
FIG. 8 is a logic flow diagram showing the reconstruction method of the present invention in one embodiment.

The logic flow diagram of FIG. 8 shows the sequence for applying artifact correction in reconstruction of the CT images according to one embodiment. This sequence corresponds generally to the processing activity of artifact reduction step 110 in FIG. 1. Initial image processing required for this sequence includes obtaining the metal-containing subset of original reconstructed CT images 702, generating high density features images 704 from that subset, and forming compensation images 804 for that subset, as described earlier.

Figure 9B:
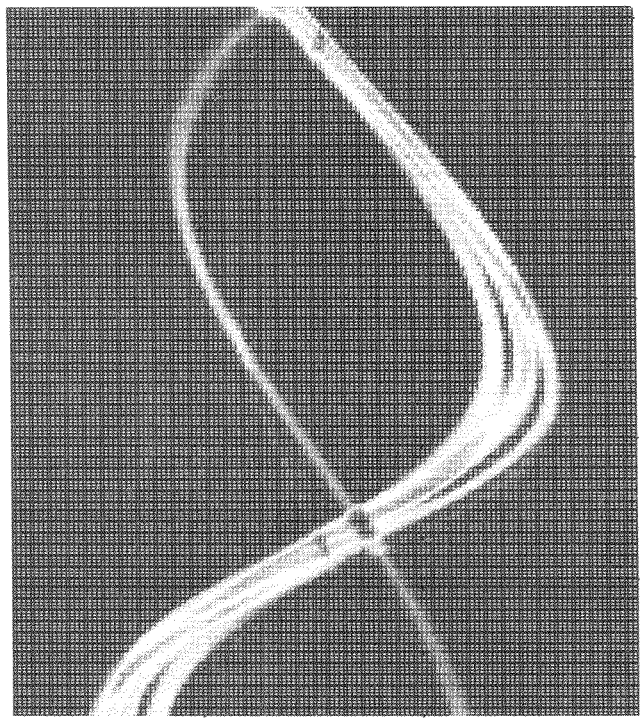
FIG. 9B is a sinogram of a high density features image.
Figure 9A:
FIG. 9A is a sinogram of an original CT image prior to correction for high density features.
Figure 9D:
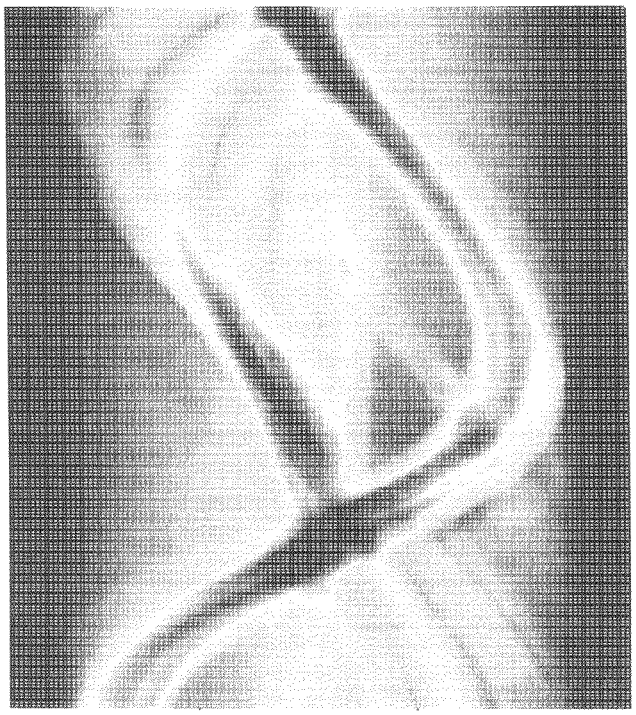
FIG. 9D is a corrected sinogram used for reconstructing a new image.
Figure 9C:
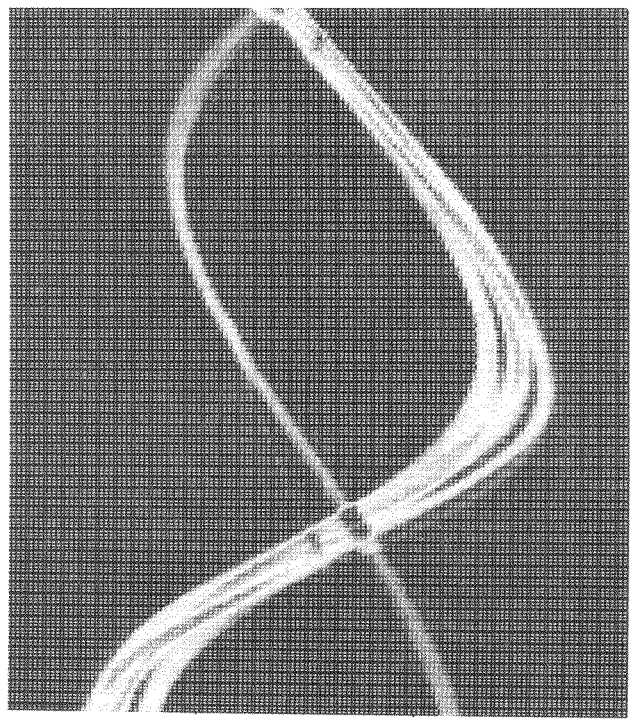
FIG. 9C is a sinogram of a compensation image.

In the sequence of FIG. 8 and referring to FIG. 9A, a sinogram W 1202 is generated in a step 302 for each original image 702 from the selected subset of input image slices, using the Radon transform that executes on a suitable image processing host. The Radon transform for forming a sinogram image and its inverse operations are computational processes familiar to those skilled in diagnostic image processing. As shown in FIG. 9B, a sinogram M 1204 is generated in a step 304 for each corresponding high density features image 704 from image data for the same selected subset of input images (corresponding to image 702 in FIGS. 3 and 10A). Likewise, as shown in FIG. 9C, a sinogram P 1206 is generated in a step 306 for each corresponding compensation image 804 from the same selected subset of input images (corresponding to image 702). In a subtraction step 308, a difference sinogram WsM is generated by subtraction of sinogram M 1204 from sinogram W 1202. In a summation step 310, compensation image sinogram P 1206 and difference sinogram WsM are then summed together to produce a final sinogram WsMaP (1208), as shown in FIG. 9D. In a processing step 312, the corrected CT image is then reconstructed by applying an inverse Radon transform to sinogram WsMaP, at each angle. Elements in sinogram WsMaP that reside in the band corresponding to that in sinogram W or P are interpolated using elements in WsMaP that lie immediately adjacent to the band boundary. As a near-final process in step 312, features in high density features image 704 are replanted back to the corresponding positions in the final reconstructed image 1102 (FIG. 10B). Boundary pixels of these features in image 1102 are smoothed out. Then, the reconstruction of the corrected CT images can be carried out in processing step 312.

Figure 10A:
FIG. 10A shows a dental CT image with high density feature artifacts.
Figure 10B:
FIG. 10B shows the dental CT image of FIG. 10A with artifact correction applied.

By way of example, FIGS. 10A and 10B show the results of reducing metal artifacts using the method of the present invention. An area 1104 in original CT image 702 shows the image of a tooth structure having a number of artifacts related to metal features in the tooth. A corresponding area 1106 in a processed image 1102 shows how the method of the present invention compensates for metal objects and mitigates artifacts by using the processing of FIG. 8. As area 1106 of FIG. 10B shows, the final reconstructed image 1102 at least partially recovers the pixels in the dark spots between the high density objects in the original image 702.

Using Prior Knowledge About The Patient

In addition to feature classification, artifact identification and suppression can he assisted by using information from patient status or history. Prior knowledge of the patient can be used to generate-one or more compensation images that can be used for recovery of missed data. Prior knowledge can include number, locations, and composition of fillings from patient history, for example.

Referring again to FIG. 5, high density features image 704 shows dental fillings identified by applying metal detection step 106 to image 702 (FIG. 3). High density features image 704 in FIG. 5 contains a number of high density object features, appearing in white in the figure. Unlike earlier methods, the detected metal object or other high density features are further classified into a number of classes. Using classification techniques on the data in FIGS. 5 and 6, feature 904 belongs to a root canal class, and feature 906 belongs to a dentine class. The criteria used for classification could alternately relate to geometric measures of the features. Accordingly, features in high density features image 704 of FIG. 5 are classified as dentine filling features. This classification is then used in a subsequent step.

Operator Interaction

Embodiments of the present invention take advantage of operator interaction for obtaining and applying useful information about the patient for improving the overall efficiency of operations such as image subset selection, classification, and other functions.

In general, only a small fraction of the cone beam volume has metal or other high density feature content. Artifact correction, which can be computationally demanding and may require considerable processing resources, need only be carried out on those images that exhibit high density features. Prior knowledge of the patient can he used in order to focus compensation activity to those portions of the image that are affected by metal and other high density objects, to facilitate classification, and to make more effective use of computing resources.

Figure 11:
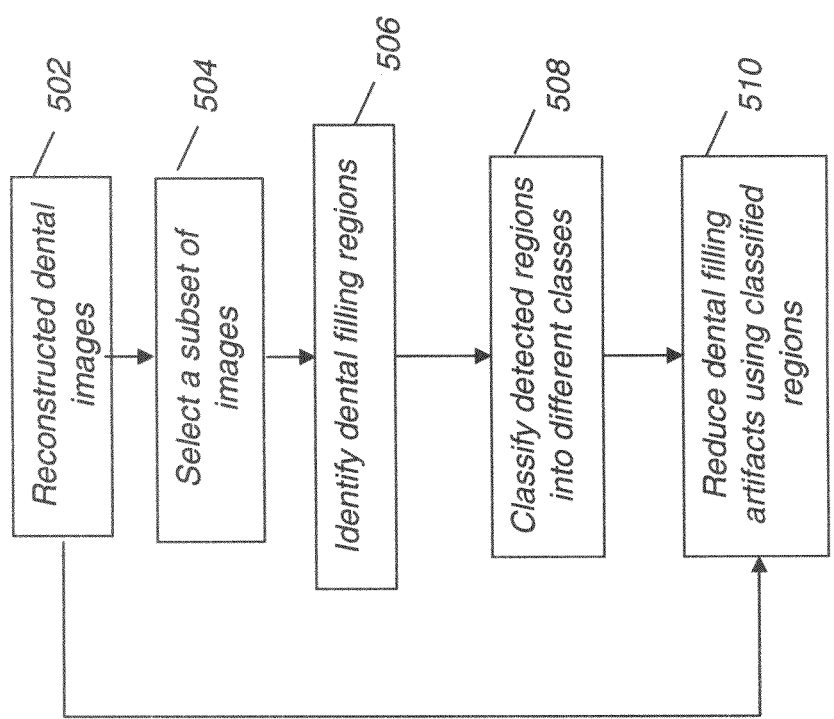
FIG. 11 is a logic flow diagram showing steps of the present invention in embodiments using operator interaction.

Referring to the logic flow sequence of FIG. 11, there is shown a process for simplifying artifact compensation where it is known to the technician or other operator that the patient has fillings. One or more reconstructed images are obtained in a step 502. A selection step 504 follows, during which prior knowledge of patient history can be put to effective use for detecting the subset of image slices to be processed. A detection step 506 then detects dental fillings or other features in the reconstructed image.

Figure 12A:
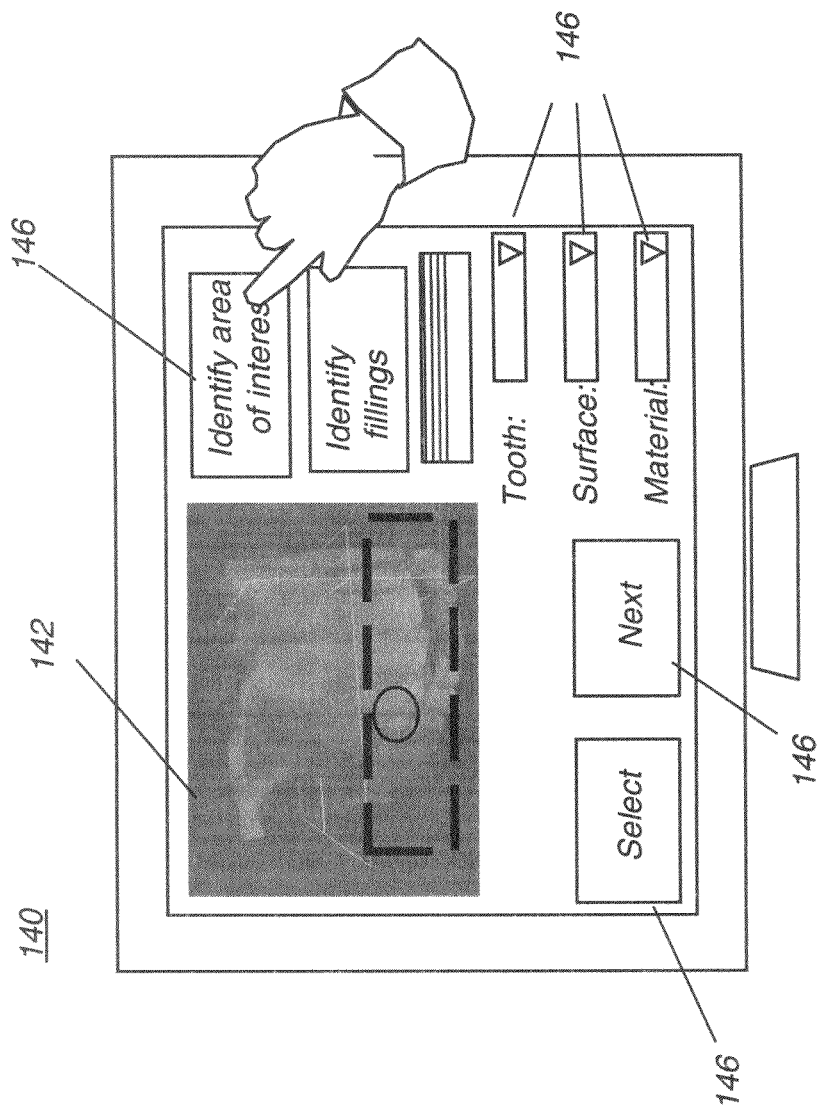
FIG. 12A is a plan view showing a touchscreen operator console with functions for selecting image areas and providing patient information for processing.

Processes of identifying the subset of images in step 504 and detecting dental fillings in step 506 can be carried out by accessing a patient history database or using an operator interface as shown in FIG. 12A. An operator console 140, shown as a touchscreen display, shows a reconstructed CT volume 142 prior to processing for metal artifact removal. Console 140 provides a number of controls 146 that enable the operator to outline an area of interest, such as by hand or using some other type of pointer, such as a mouse or other cursor manipulation device that defines those portions of the reconstructed image that are of interest for high density artifact compensation. In the example shown, the operator can define the feature, region, or area of interest that effectively selects the subset of image slices needed in selection step 504 of FIG. 11. The operator can also list and indicate individual fillings or other high density features, such as using the menu-driven interface shown, thus performing the function of detection step 506 in FIG. 11.

Figure 12B:
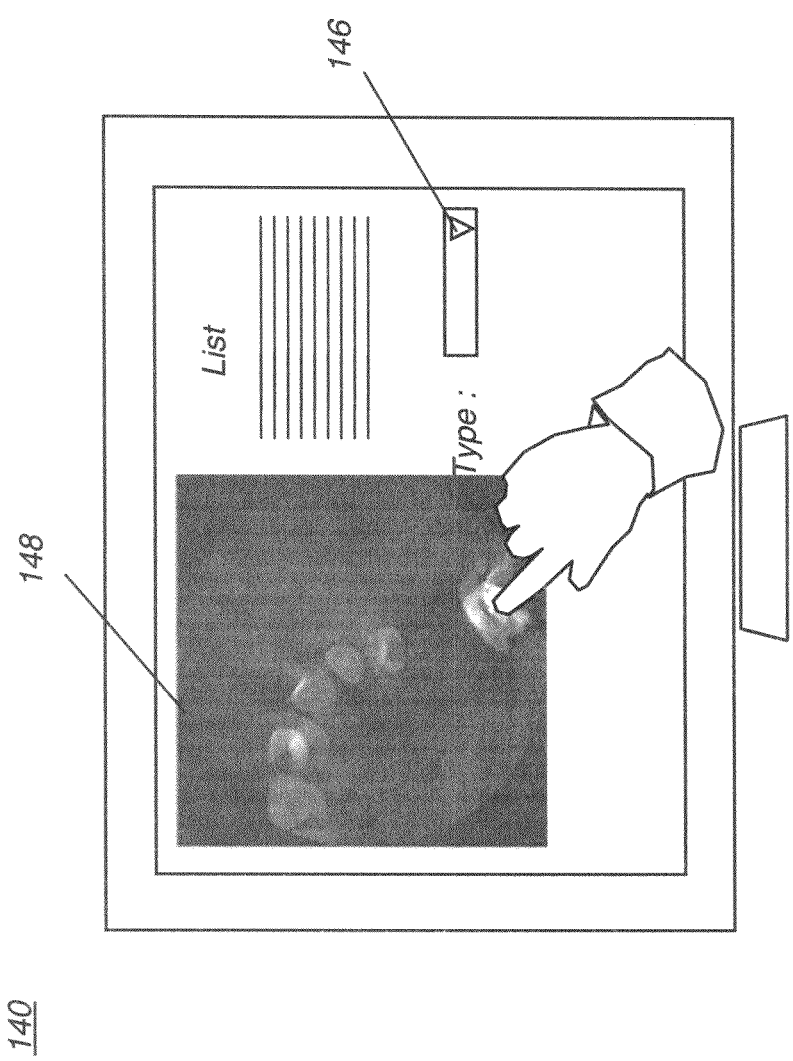
FIG. 12B is a plan view showing a touchscreen operator console with functions for providing information used for classification.

FIG. 12B shows operator console 140 used for operator-assisted classification of high density features and surrounding tissues from a displayed reconstructed image 148. It should be emphasized that FIGS. 12A and 12B are given by way of example only; any number of operator interface utilities could be used for the purpose of identifying the subset of images in step 504, detecting dental filling and other features or regions in step 506, and classifying detected features in a classification step 508, as shown in FIG. 11. As a result of operator-assisted identification and detection functions, artifacts resulting from high density features can be reduced in generating reconstructed images in a reconstruction step 510.

Embodiments of the present invention provide a practical metal artifacts reduction system in which it can be advantageous to synergistically integrate the skills of the human operator of the system with the power of the computer in the process of metal artifacts reduction. This takes advantage of human skills of creativity, use of heuristics, flexibility, and judgment, and combines these with computer advantages, such as speed of computation, capability for exhaustive and accurate processing, reporting and data access and storage capabilities, and display flexibility.

In one embodiment, the present invention utilizes a computer program with stored instructions that perform metal artifacts reduction on image data accessed from an electronic memory in accordance with the method described. The stored instructions configure the computer to form a processor that performs the metal artifacts reduction processing. As can be appreciated by those skilled in the image processing arts, a computer program of an embodiment of the present invention can be utilized by a suitable, general-purpose computer system, such as a personal computer or workstation. However, many other types of computer systems or programmed logic processors can be used to execute the computer program of the present invention, including networked processors. The computer program for performing the method of the present invention may be stored in a computer readable storage medium. This medium may comprise, for example; magnetic storage media such as a magnetic disk (such as a hard drive) or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It is noted that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may he selected from such algorithms, systems, hardware, components and elements known in the art. The computer hardware can also maintain a library or database of information that can be indexed and selected for use under specified conditions, such as maintaining a library of suitable tissue images for use in forming reconstructed image 804 (FIG. 7) for example.

The invention has been described in detail with particular reference to presently preferred embodiments, but it will be understood that variations and modifications can be effected that are within the scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST 102 reconstructed volume
104 image selection step
106 detection step
108 classification step
110 artifact reduction step
112 reconstructed volume
140 operator console
142 CT volume
146 control
148 reconstructed image
202 computation step
204 ratio computation step
206 evaluation step
302 step
304 step
306 step
308 subtraction step
310 summation step
312 processing step
502 step
504 selection step
506 detection step
508 classification step
510 reconstruction step
702 original CT image
704 high density features image
804 compensation image
902 display
904 feature in dentine region
906 feature in root cannel region
1002 graph of order statistics
1102 reconstructed ct image
1104 area
1202 sinogram W
1204 sinogram M
1206 sinogram P
1208 sinogram WsMaP

The invention claimed is:

1. A method of providing a corrected reconstructed computed tomography image comprising:
accessing image data for a plurality of computed tomography images of a subject;
identifying a subset of the computed tomography images that comprise one or more high density features;
detecting, in each of the identified subset of computed tomography images, at least one high density feature;
classifying the at least one high density feature according to one or more feature characteristics;
forming one or more compensation images by substituting pixels representative of tissue over the at least one classified high density feature;
computing a compensation sinogram P using the one or more compensation images;
generating a difference sinogram WsM for each image in the identified subset of computed tomography images by subtracting a first sinogram M of the at least one classified high density feature from a second sinogram W of the original image;
generating a resultant sinogram WsMaP for each image in the identified subset of computed tomography images by adding the compensation sinogram P to the difference sinogram WsM; and
forming the corrected reconstructed computed tomography image according to the resultant sinogram WsMaP generated for each image in the identified subset of computed tomography images.

2. The method of claim 1 wherein identifying the subset of the computed tomography images that comprise high density features comprises accepting one or more operator instructions entered according to a displayed original reconstructed image.

3. The method of claim 1 wherein classifying the at least one high density feature comprises accepting one or more operator instructions entered according to a displayed original reconstructed image.

4. The method of claim 1 wherein identifying the subset of the computed tomography images that comprise one or more high density features comprises arranging image data as order statistics.

5. The method of claim 1 wherein the one or more high density features comprises a metallic object.

6. The method of claim 1 wherein forming the one or more compensation images comprises obtaining representative pixels from one or more-stored images.

7. The method of claim 1 wherein the computed tomography images are obtained from a cone beam x-ray scanner.

8. The method of claim 1 wherein detecting the at least one high density feature comprises applying a threshold value.

9. The method of claim 1 wherein classifying the at least one high density feature according to one or more feature characteristics comprises utilizing one or more of position or dimension for the high density feature.

10. The method of claim 1 wherein classifying the at least one high density feature comprises identifying tissue surrounding the high density feature as one of enamel, dentine, root, and bone.

11. The method of claim 1 further comprising displaying the reconstructed computed tomography image.

12. The method of claim 1 wherein identifying the subset of the computed tomography images that contain one or more high density features comprises using prior knowledge about the subject.

13. The method of claim 1 wherein identifying the subset of the computed tomography images that comprise one or more high density features comprises identifying at least one of the computed tomography images of the subject from the plurality of computed tomography images as a candidate computed tomography image and executing a sequence of:
a) arranging pixel values in the identified candidate computed tomography image as order statistics;
b) selecting the identified candidate computed tomography image as member of the subset of the computed tomography images that contain one or more high density features according to one or more values obtained from the order statistics; and
c) identifying another of the computed tomography images of the subject from the plurality of computed tomography images as the next candidate computed tomography image and repeating steps a) and b).

14. The method of claim 13 wherein the one or more values obtained from the order statistics comprises a ratio.

15. The method of claim 13 wherein the one or more values obtained from the order statistics comprises a ratio of one or more of the order statistics to a maximum pixel value within the candidate computed tomography image.

16. A method of providing a corrected reconstructed computed tomography image comprising:
- accessing image data for a plurality of computed tomography images of a subject;
- identifying a subset of the computed tomography images that comprise one or more high density features according to an arrangement of image values as order statistics;
- detecting, in each of the identified subset of computed tomography images, at least one high density feature;
- classifying the at least one high density feature according to one or more feature characteristics;
- forming one or more compensation images by substituting pixels representative of tissue over the at least one classified high density feature;
- computing a compensation sinogram P using the one or more compensation images;
- generating a difference sinogram WsM for each image in the identified subset of images by subtracting a first sinogram M of the at least one high density feature from a second sinogram W of the original image;
- generating a resultant sinogram WsMaP for each image in the identified subset of images by adding the compensation sinogram P to the difference sinogram WsM;
- forming the corrected reconstructed computed tomography image according to the resultant sinogram WsMaP generated for each image in the identified subset of images; and
- displaying the reconstructed computed tomography image.

* * * * *